(12) United States Patent
Nadeau et al.

(10) Patent No.: US 10,438,346 B2
(45) Date of Patent: Oct. 8, 2019

(54) METHOD FOR EXTRACTION OF SPATIAL FREQUENCY INFORMATION FOR QUANTITATIVE TISSUE IMAGING

(71) Applicant: The Regents of the University of California, Oakland, CA (US)

(72) Inventors: Kyle Nadeau, Irvine, CA (US); Anthony J. Durkin, Irvine, CA (US); Bruce J. Tromberg, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 99 days.

(21) Appl. No.: 15/108,279

(22) PCT Filed: Jan. 6, 2015

(86) PCT No.: PCT/US2015/010278
§ 371 (c)(1),
(2) Date: Jun. 24, 2016

(87) PCT Pub. No.: WO2015/105780
PCT Pub. Date: Jul. 16, 2015

(65) Prior Publication Data
US 2016/0300348 A1    Oct. 13, 2016

Related U.S. Application Data

(60) Provisional application No. 61/924,401, filed on Jan. 7, 2014.

(51) Int. Cl.
*G06K 9/00*        (2006.01)
*G06T 7/00*        (2017.01)
*G01B 11/25*      (2006.01)
*A61B 1/06*        (2006.01)
(Continued)

(52) U.S. Cl.
CPC .............. *G06T 7/0012* (2013.01); *A61B 1/06* (2013.01); *G01B 11/25* (2013.01); *G06K 9/4604* (2013.01);
(Continued)

(58) Field of Classification Search
None
See application file for complete search history.

(56) References Cited

U.S. PATENT DOCUMENTS

| | | |
|---|---|---|
| 5,299,148 A | 3/1994 | Gardner et al. |
| 2004/0039379 A1 | 5/2004 | Viator et al. |

(Continued)

OTHER PUBLICATIONS

Konecky, et al., "Spatial Frequency Domain Tomography of Protoporphyrin IX Flourescence in Preclinical Glioma Models," Journal of Biomed Optics, 17, 056008 (2012).
(Continued)

*Primary Examiner* — Atiba O Fitzpatrick
(74) *Attorney, Agent, or Firm* — Accelerator AIX; Sean D. Senn

(57) ABSTRACT

The present invention relates to methods and devices that may be used to extract spatial frequency information. In one embodiment, the invention provides an instrument configured to extract data using a two-dimensional (2D) Hilbert transform technique, and providing spatial frequency information from a sample. In another embodiment, the invention provides a spatial frequency domain imaging (SFDI) device adapted for demodulation using two or less imaging frames.

22 Claims, 12 Drawing Sheets

(51) Int. Cl.
  *G06K 9/46* (2006.01)
  *G06T 7/50* (2017.01)
  *G06T 7/521* (2017.01)
  *G06T 7/42* (2017.01)
(52) U.S. Cl.
  CPC .................. *G06T 7/42* (2017.01); *G06T 7/50* (2017.01); *G06T 7/521* (2017.01); *G06T 2207/10068* (2013.01); *G06T 2207/30004* (2013.01)

(56) References Cited

U.S. PATENT DOCUMENTS

| | | |
|---|---|---|
| 2006/0120621 A1 | 6/2006 | Larkin et al. |
| 2006/0184043 A1 | 8/2006 | Tromberg et al. |
| 2008/0100836 A1 | 5/2008 | Hagler |
| 2008/0101657 A1 | 5/2008 | Durkin et al. |
| 2009/0118622 A1* | 5/2009 | Durkin .................. A61B 5/0073 600/473 |
| 2013/0336551 A1* | 12/2013 | Clingman ............ A61B 5/0095 382/128 |

OTHER PUBLICATIONS

Cuccia, D.J., et al.,"Modulated imaging: quantitative analysis and tomography of turbid media in the spatial frequency domain," Optics Lett, 30(11) 1354-6, (2005).

Cuccia, D.J., et al., "Quantitation and mapping of tissue optical properties using modulated imaging," Journal Biomed Optics, 14(2) 024012, (2009).

Konecky S.D., et al., "Imaging scattering orientation with spatial frequency domain imaging", Journal Biomed Optics, 16(12), 126001, (2011).

Larkin, K.G., et al., "Natural demodulation of two-dimensional fringe patterns. I. General background of the spiral phase quadrature transform, J Opt Soc Am A Opt Image Sci Vis," 18(8), 1862-70 (2001).

Larkin, K.G., "Natural demodulation of two-dimensional fringe patterns II, Stationary phase analysis of the spiral phase quadrature transform," J Opt Soc Am A Opt Image Sci Vis, 18(8) 1871-81, (2001).

Gioux, S., et al., "Three-dimensional surface profile intensity correction for spatially modulated imaging," Journal Biomed Optical, 14(3) 034045, (2009).

Cuccia, D.J. Spatial Frequency Domain Imaging (SFDI) "A technology overview and validation of an LED-based clinic friendly device," in Photonics West, BiOS, San Francisco, CA: SPIE, (2012).

Konecky, et al., "Quantitative optical tomography of sub-surface heterogeneities using spatially modulated structure light," Opt Express, 17, 14780-90 (2009).

* cited by examiner

METHOD FOR EXTRACTION OF SPATIAL FREQUENCY INFORMATION FOR QUANTITATIVE TISSUE IMAGING

CROSS REFERENCE TO RELATED APPLICATIONS

This application is a National Phase of International Application No. PCT/US2015/010278, filed Jan. 6, 2015, which designated the U.S. and that International Application was published under PCT Article 21(2) in English. This application also includes a claim of priority under 35 U.S.C. § 119(e) to U.S. Provisional Application No. 61/924,401, filed Jan. 7, 2014, the entirety of which is hereby incorporated by reference.

GOVERNMENT RIGHTS

This invention was made with Government support under Grant Nos. EB014440 and EB015890, awarded by the National Institutes of Health. The Government has certain rights in this invention.

FIELD OF THE INVENTION

The invention relates to the field of optics and more specifically, extraction of data and information.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

There are various optical imaging tools and methods that may be used in conjunction with biomedical diagnostics and treatments. For example, Diffuse Optical Spectroscopic Imaging (DOSI) is a technique that can quantify absorption and scattering coefficients of tissues up to several centimeters deep. Or, for example, SFDI (Spatial Frequency Domain Imaging) is a quantitative optical imaging modality that employs spatially-modulated to separate light scattering from absorption in its measurements. Unlike DOSI, SFDI is a wide-field optical technique, and works by taking advantage of the Fourier inverse of point source-detector measurements by projecting light into spatially sinusoidal patterns onto a sample such as a tissue sample. In turn, absorption and scattering quantification can give information about the sample, where by analyzing the spatial modulation transfer function for the diffusion of light within the tissue, both depth and quantifiable optical properties can be extracted for various practical applications. However, currently available optical imaging techniques are also not without their limitations and disadvantages. For example, limited speed is an issue in SFDI, where there is a need for multiple frames of data, and there are difficulties in increasing data acquisition speed to the frame-rate of a camera. Thus, there is a need in the art for more effective optical imaging devices and methods.

SUMMARY OF THE INVENTION

Various embodiments include a method of extracting spatial frequency information, comprising utilizing an instrument configured to provide a dataset from a sample, and extracting the dataset for spatial frequency information from the sample illuminated by a single pattern projection by filtering and/or transforming the image data collected from the sample. In another embodiment, transforming the image data includes utilizing a spiral phase function in 2D Fourier space. In another embodiment, transforming the image data comprises a 2D Hilbert transform technique. In another embodiment, the instrument comprises a structured illumination device. In another embodiment, the structured illumination device comprises a Spatial Frequency Domain Imaging (SFDI) device. In another embodiment, the spatial frequency information comprises optical properties of the sample. In another embodiment, the spatial frequency information comprises structural orientation contrast of the sample. In another embodiment, the sample is a biological sample. In another embodiment, the sample is in vivo tissue. In another embodiment, the sample is turbid media. In another embodiment, the spatial frequency information is extracted directly from a subject. In another embodiment, the spatial frequency information is extracted from a human. In another embodiment, the spatial frequency information is extracted from an animal. In another embodiment, the spatial frequency information is extracted from a plant. In another embodiment, the spatial frequency information is extracted from an organism. In another embodiment, a single frame of data corresponds to each AC spatial frequency. In another embodiment, the spatial frequency information is extracted from rotated sinusoidal patterns. In another embodiment, the spatial frequency information includes tissue structural orientation.

Other embodiments include a method of acquiring and processing data for optical properties, comprising acquiring both an AC/DC image frame and a DC image frame of a target, removing a DC component from the AC/DC frame of the target, and acquiring and processing data for optical properties by demodulating an AC component. In another embodiment, removing the DC component is a subtractive method. In another embodiment, removing the DC component includes a method of wavelet filtering and/or frequency thresholding in the spatial frequency domain. In another embodiment, demodulating the AC component comprises applying the AC component to a 2D Hilbert transform kernel. In another embodiment, the method further comprises more than two spatial frequency components. In another embodiment, the method further comprises a capability for depth localization. In another embodiment, the method further comprises a capability for improving optical property fitting. In another embodiment, the method further comprises a capability for rapid switching between spatial frequencies. In another embodiment, the capability for rapid switching between spatial frequencies includes the use of a linear translation stage. In another embodiment, the capability for rapid switching between spatial frequencies includes movement of a printed mask and/or lens. In another embodiment, acquiring both the AC/DC frame and the DC frame of the target includes an electronic spatial light modulator toggling between planar and structured patterns. In another embodiment, acquiring both the AC/DC frame and the DC frame of the target includes a rotating disc with printed DC and sinusoidal patterns. In another embodiment, acquiring both the AC/DC frame and the DC frame of the target includes a linear translation stage with printed DC/sinusoidal patterns. In another embodiment, the method is further described in FIG. 8 herein. In another embodiment, the target is a turbid medium.

Other embodiments include a method of acquiring and processing data, comprising acquiring multiple AC/DC image frames with different orientation angles of a target, removing a plurality of DC components from the multiple AC/DC image frames by using a signal processing technique and/or subtracting using a dedicated DC frame, and acquiring and processing data for spatial orientation of target properties by demodulating one or more AC components. In another embodiment, demodulating one or more AC components comprises filtering and/or transforming an AC component. In another embodiment, transforming the one or more AC components comprises applying an AC component to a 2D Hilbert transform kernel. In another embodiment, acquiring multiple AC/DC image frames with different orientation angles of the target includes use of an electronic spatial light modulator. In another embodiment, acquiring multiple AC/DC image frames with different orientation angles of the target includes a rotating disc with printed sinusoidal pattern. In another embodiment, spatial frequency is rapidly switched using a translation stage setup. In another embodiment, the target is a turbid medium.

Various embodiments include an apparatus, comprising means for projecting spatially modulated light on a target, and means for extracting spatial frequency information from the sample using a two-dimensional (2D) Hilbert transform technique. In another embodiment, the means for projecting spatially modulated light comprises a Spatial Frequency Domain Imaging (SFDI) device. In another embodiment, the apparatus further comprises an endoscope. In another embodiment, the apparatus is described as FIG. 9 herein. In another embodiment, the apparatus is described as FIG. 10 herein. In another embodiment, the apparatus is described as FIG. 11 herein. In another embodiment, the apparatus further comprises a real-time SFDI platform.

Other embodiments include an imaging apparatus, comprising a spatial frequency domain imaging (SFDI) device adapted for demodulation using a single imaging frame. In another embodiment, the SFDI device is demodulated by applying a Hilbert transform technique to SFDI frames. In another embodiment, the imaging frames include modulation patterns that have an arbitrary directionality with respect to lateral imaging axes (x,y). In another embodiment, the SFDI device is modified for real-time imaging. In another embodiment, the data acquisition time is reduced relative to conventional SFDI data acquisition time. In another embodiment, the apparatus further comprises a capability of information extraction using multi-frequency synthesis. In another embodiment, the SFDI device is further adapted to produce reflectance maps that provide optical calculations of a biological tissue sample. In another embodiment, the SFDI device includes a mechanical object for light modulation. In another embodiment, the SFDI device may be used to diagnose a disease. In another embodiment, the SFDI device may be used for quantitative analysis of tissue composition and/or change in composition.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 14 depicts, in accordance with embodiments herein, demodulated reflectance images at 0.2 mm−1 of a tissue-simulating phantom using (a) conventional, 3-phase SFDI (4 frames), and (b) the advanced, Hilbert-based technique (2 frames). (c) Map of percent difference in demodulated reflectance between 3-phase SFDI and the Hilbert-based technique. (d) Plot of mean diffuse reflectance vs. spatial frequency for the region of interest (ROI), shown in a.

DESCRIPTION OF THE INVENTION

Figure 1:
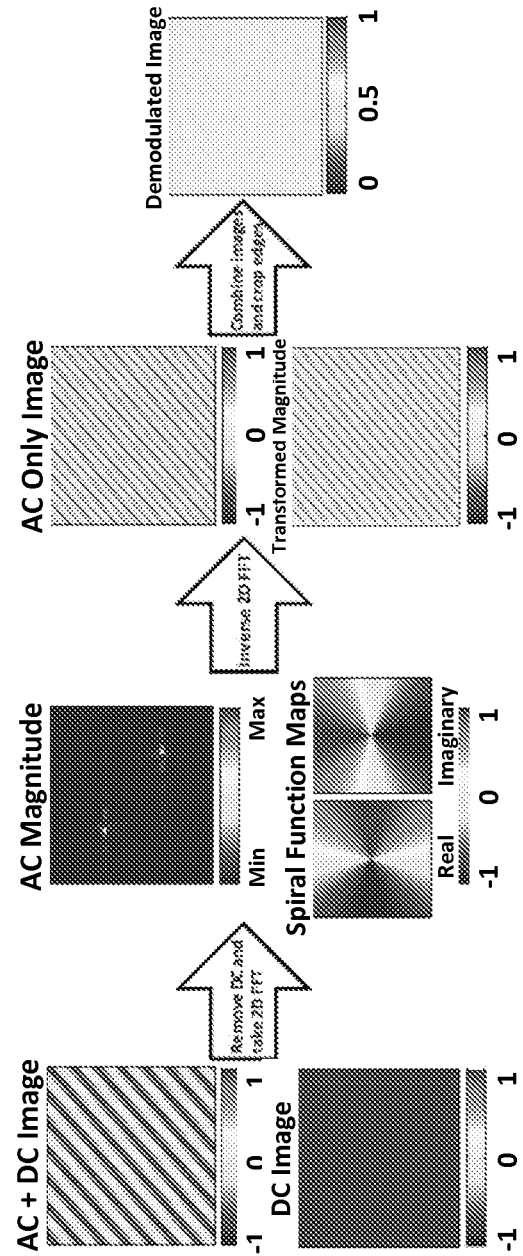
FIG. 1 depicts, in accordance with embodiments herein, two-dimensional Hilbert demodulation method. First, the DC component of the modulated image is removed, and a fast Fourier transform (FFT) is performed on the image. The resulting two-dimensional map in Fourier space is then multiplied by a spiral function. In inverse FFT is performed on the map, resulting in an image whose magnitude is the original modulated image phase-shifted by 90 degrees. This image is multiplied by the imaginary unit and added to the original image. The magnitude of this image results in the demodulated diffuse reflectance.

All references cited herein are incorporated by reference in their entirety as though fully set forth. Unless defined otherwise, technical and scientific terms used herein have the same meaning as commonly understood by one of ordinary skill in the art to which this invention belongs. Brady et al., Optical Imaging and Spectroscopy, Wiley-OSA (2009); Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); and Advanced Organic Chemistry Reactions, Mechanisms and Structure 7th ed., J. Wiley & Sons (New York, N.Y. 2013), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

References hereby incorporated by reference include and are not limited to the following: Duarte, et al., "Single-pixel imaging via compressive sampling," IEEE Signaling Processing Magazine, March 2008; Saager, et al., "Determination of optical properties of turbid media spanning visible and near-infrared regimes via spatially modulated quantitative spectroscopy," Journal of Biomedical Optics 15(1), January/February 2010; and Konecky, et al., "Quantitative optical tomography of sub-surface heterogeneities using spatially modulated structured light," Optics Express, Vol. 17, No. 17, Aug. 5, 2009.

As used herein, the abbreviation "SFDI" means Spatial Frequency Domain Imaging.

As used herein, the abbreviation "CCD" means Charged Coupled Device.

As used herein, the abbreviation "MSE" means multi-frequency synthesis and extraction.

As disclosed herein, the inventors have developed a method for extracting spatial frequency information content from biological tissue, which in one embodiment, may be used to calculate tissue optical properties and determine tissue structural orientation. This demodulation method employs a 2D Hilbert transform using a spiral phase function in Fourier space. In another embodiment, the approach allows for the determination of tissue optical properties using a single frame of data for each modulation frequency, increasing imaging speed by two-to-threefold versus conventional, 3-phase spatial frequency domain imaging (SFDI). In another embodiment, the single-phase Hilbert transform approach recovers optical property and scattering orientation index (SOI) values within 1% and 10% of 3-phase SFDI, respectively. These results demonstrate that using the Hilbert demodulation technique, SFDI data acquisition speed can be increased significantly while preserving data quality, which will allow the implementation of a real-time SFDI platform.

As further described herein, the inventors have developed a demodulation approach, where various methods were developed for extracting information content from SFDI images using fewer frames of data than the established technique. The need for multiple frames of data is often the bottleneck and challenge in SFDI workflow, including in moving to real-time SFDI. In accordance with various embodiments herein, it has the added benefit of being able to accommodate SFDI frames with rotated patterns, which may be used to probe tissue orientation.

In one embodiment, the present invention provides for a method of extracting spatial frequency information, comprising utilizing an instrument configured to provide a dataset from a sample, and extracting the dataset for spatial frequency information from the sample illuminated by a single pattern projection by filtering and/or transforming the image data collected from the sample. In another embodiment, the present invention provides an imaging apparatus, comprising a spatial frequency domain imaging (SFDI) device adapted for demodulation using two or less imaging frames. In another embodiment, the SFDI device is adapted for demodulation using one imaging frame. In another embodiment, the SFDI device is demodulated by applying a Hilbert transform technique to SFDI frames. In another embodiment, the imaging frames include modulation patterns that have an arbitrary directionality with respect to lateral imaging axes (x,y). In another embodiment, the SFDI device is modified for real-time imaging. In another embodiment, the data acquisition time is reduced relative to conventional SFDI data acquisition time. In another embodiment, the apparatus further comprises a capability of information extraction using multi-frequency synthesis. In another embodiment, the SFDI device is further adapted to produce reflectance maps that provide optical calculations of a biological tissue sample. In another embodiment, the SFDI device includes a mechanical object for light modulation.

In one embodiment, the present invention provides a method of imaging a sample and/or biological tissue sample, comprising providing a spatial frequency domain imaging (SFDI) device adapted for demodulation using two or less imaging frames, and visualizing and/or projecting a biological tissue sample through the SFDI device adapted for demodulation using two or less imaging frames. In another embodiment, the SFDI device may be used to analyze physical properties of the tissue. In another embodiment, the data acquisition speed is increased to the frame rate of a camera. In another embodiment, the SFDI modulation patterns and diffuse reflectance maps are acquired at one or more angles so that the orientation angle and magnitude of structures in the biological sample may be determined.

In one embodiment, the present invention provides a method of diagnosing a disease in a subject, comprising providing a sample from a subject, using an optical imaging apparatus comprising a spatial frequency domain imaging (SFDI) device adapted for demodulation using two or less imaging frames to analyze the physical properties of the sample, and diagnosing the disease based on the physical properties of the sample. In another embodiment, the physical properties of the sample include tissue biological function at high temporal resolution, including hemodynamics and chemical constituents. In another embodiment, the subject is human.

In one embodiment, the present invention provides a method of prognosing a disease in a subject, comprising providing a sample from a subject, using a spatial frequency domain imaging (SFDI) device adapted for demodulation using two or less imaging frames to analyze the physical properties of the sample, and prognosing a severe form of the disease based on the physical properties of the sample. In another embodiment, the physical properties of the sample include tissue biological function at high temporal resolution, including hemodynamics and chemical constituents. In another embodiment, the method of prognosing further comprises an analysis of time to heal from the disease. In another embodiment, the subject is human.

As further described herein, the inventors created a 2D Hilbert demodulation method on a highly reflecting surface. First, the DC component of the modulated image is removed, and a fast Fourier transform (FFT) is performed on the AC+DC image. The resulting 2D map in Fourier space is then multiplied by a spiral phase function, consisting of a continuous, radially-varying map ranging in value from −1 to +1 in real and imaginary space. An inverse FFT is performed on the map, resulting in an image whose magnitude is the original modulated image phase-shifted by 90 degrees. This image is multiplied by the imaginary unit and added to the original image. The magnitude of this image results in the demodulated diffuse reflectance of the AC component from the original AC+DC image. In accordance with various embodiments herein, the present invention provides a method of acquiring and processing data for optical properties, comprising acquiring both an AC/DC image frame and a DC image frame of a target, removing a DC component from the AC/DC frame of the target, and acquiring and processing data for optical properties by demodulating an AC component. In another embodiment, the target is a turbid medium.

As used herein, the term "sample" is not in any way only limited to biological samples that are taken from and analyzed apart from an individual. A sample may include, for example, a target to be analyzed and/or visualized while it is still part of a living individual, such as visualizing and/or analyzing a body part such as an arm, or muscle tissue, of an individual.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Not withstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Background

The inventors addressed the fundamental data acquisition rate limitation in spatial frequency domain imaging (SFDI). SFDI is a quantitative optical imaging modality that employs spatially-modulated to separate light scattering from absorption in its measurements. Currently, a minimum of four images are required to extract the necessary information from the sample. However, for certain applications, such as probing the structural orientation of tissue, several more frames of data are required. The need for multiple frames of data is the primary bottleneck in the SFDI workflow. In order to move towards real-time SFDI, this issue must be addressed. One solution to SFDI demodulation is a 3-phase technique. The disadvantage to this technique is that, in order to extract information from each spatial frequency, three frames of data are required. However, this limits the speed at which SFDI can be performed.

Example 2

Features

In accordance with embodiments herein, the demodulation technique may be used to perform real-time SFDI and scattering orientation imaging. Some of the features for the developed technique include:
  i. Reduction in number of frames reduces data acquisition time by one half to two thirds. SFDI data processing has been described in detail previously. Currently, SFDI requires a minimum of four frames of data to generate maps of tissue optical properties. These images include a planar (DC) image, and three phase-offset, modulated (AC) images. With the inventors' approach, it has been shown a reduction in the number of AC frames required from three to one, thus reducing the total minimum required images from four to two, reducing data acquisition time by ½. Using this new technique, the number of frames required decreases more if more spatial frequencies are used. Since only one frame is required for each spatial frequency, the amount of frames required approaches ⅓ of that from conventional SFDI if many spatial frequencies are used.
  ii. This method does not require precise phase-shifting of the modulated light, allowing for new modulation methods, which reduce hardware costs and further reduce data acquisition time. Conventional SFDI requires images taken at three specific, relative phases (0, 120, 240 degrees) for each modulation frequency. This phase-mapping requirement necessitates light modulation hardware with high precision, such as a digital micromirror device (DMD). These devices introduce an additional limitation to data acquisition time, since they have refresh rates. Therefore, it is often limited by the refresh rate of these modulators with respect to single frame acquisition time. In addition, state of the art SLM's may be expensive, costing in the thousands or tens of thousands of dollars. Since the developed demodulation technique only requires a single AC image, mechanical objects may be used for light modulation. The inventors have demonstrated the ability to demodulate SFDI data modulated using a static mechanical object.
  iii. Ability to process oriented patterns reduces SFD orientation imaging time by two thirds. One feature of this developed technique is its ability to demodulate AC frames whose modulated pattern is oriented, or rotated, at an arbitrary angle. Other demodulation techniques, such as the 1D Hilbert transform, are unable to demodulate these patterns properly, since they are insensitive to the spatial orientation of the modulating pattern. Rotating modulated patterns has been used previously to evaluate the structural orientation of a variety of samples including chicken breast and rat brain. The inventors have shown that, using the developed technique, orientation contrast can be obtained comparable to conventional SFDI.

Example 3

Hilbert Demodulation Technique

In accordance with various embodiments herein, the modulated reflectance images obtained in SFDI can be described by:

$$I(x,y)=0.5*R_{DC}(x,y)+0.5M(x,y) \tag{1}$$

Where $$M(x,y)=R_{AC}(x,y)*\cos\{2\pi f_{x,y}+\varnothing(x,y)\} \tag{2}$$

The purpose of demodulation is to extract the modulated diffuse reflectance term $R_{AC}(x, y)$ from the detected amplitude $1(x, y)$. Using Euler's theorem, a cosine function can be expressed as the sum of two complex exponentials, or sidebands in the frequency domain. The Hilbert transform is a mathematical tool that can be used to obtain a single side-banded signal from a double side-banded signal such as a cosine. This allows for straightforward demodulation, since the magnitude of a single side-banded signal results is the diffuse reflectance the inventors wish to obtain. This new demodulation approach applies a two-dimensional Hilbert transform to SFDI frames using a spiral phase function in spatial frequency space, which has been used previously to demodulate closed-fringe patterns. One aspect of this approach is that it can demodulate frames whose modulation patterns are arbitrarily oriented. That is, the wavenumber of the modulating pattern can have an arbitrary directionality with respect to the lateral imaging axes (x,y). This is accomplished by applying a spiral phase function to the image in two-dimensional Fourier space. The spiral function is described as $$S(u, v) = \frac{u + iv}{\sqrt{u^2 + v^2}} \tag{3}$$

Where u and v are the lateral coordinates in two-dimensional Fourier space Eq. 3 is multiplied by the AC component, Eq. 2 (M(x, y)), of the SFDI image in two-dimensional Fourier space. This product transforms the modulating "cosine" term into a "sine" term. Next, this product is inverse Fourier transformed. Then, the magnitude is taken, which accounts for the complex contribution of the transformed map due to orientation. This is shown in Eq. 5. Finally, this term is multiplied by the complex unit and added to the AC component of the original image, and the resulting magnitude is the demodulated AC diffuse reflectance. This is shown in Eq. 4.

$$R(x,y)=|M(x,y)+iH(x,y)| \quad (4)$$

Where $$H(x,y)=|F^{-1}\{M(u,v)*S(u,v)\}| \quad (5)$$

A walkthrough of this technique using a simulated DC and AC+DC image is shown in FIG. 1. All data processing and computation used to produce data in this manuscript was performed using the MATLAB software suite (MATLAB and Statistics Toolbox Release 2011b, The MathWorks, Inc, Natick, Massachusetts). Here, the inventors begin with a DC image with a uniform intensity of 1, and an AC+DC image with an intensity varying from 0 to 1, with a modulation pattern oriented diagonally. First, the DC component is removed from the AC+DC image, and an FFT is performed on the resulting image. Next, the spatial frequency map of the DC-corrected, transformed image is multiplied with the complex spiral function map. The resulting map is then FFT inverted, and the magnitude is taken. This "magnitude" image is then multiplied by the imaginary unit, added to the DC-corrected, AC image. The magnitude of this sum results in the demodulated AC diffuse reflectance, which is uniform at an intensity of approximately 0.5.

Example 4

Advantages and Applications

In accordance with various embodiments herein, there are many advantages of the developed demodulation techniques. For example, modulated light can be used in the SFDI workflow to correct for surface curvature artifacts in diffuse reflectance measurements. In order to correct for surface curvature, a 3-phase approach has been used. Using the developed technique, it is possible to perform a profilometry measurement using 1 frame instead of 3. Phase angle maps are derived by taking the inverse tangent of ratio of the imaginary to the real component of the sum of the two terms shown in Eq. 4. This relationship is shown below in Eq. 6.

$$phaseAngle(x, y) = \tan^{-1}\frac{\text{imag}\{M(x, y) + iH(x, y)\}}{\text{real}\{M(x, y) + iH(x, y)\}} \quad (6)$$

Another application is in the extraction of individual spatial frequency components from a modulation pattern containing multiple AC spatial frequencies. The relationship that governs this concept is shown in Eq. 7. Here, the left column represents a series of diffuse reflectance intensity images taken using "p" unique projections of the multi-frequency pattern. The center matrix represents the Fourier coefficients for each image in the left column. For each spatial frequency component,($k_x$, $k_y$), the magnitude and phase of the modulating pattern are defined. The column on the right represents the demodulated diffuse reflectance maps for each spatial frequency component. In order to solve for this, one can take the inverse of the Fourier coefficient matrix, and multiply by the "intensity" column.

$$\begin{pmatrix} I_1(x,y) \\ \vdots \\ I_p(x,y) \end{pmatrix} = \quad (7)$$

-continued $$\begin{pmatrix} C_1(k_x^1, k_y^1)e^{-i(k_x^1 x+k_y^1 y)} & \cdots & C_1(k_x^N, k_y^M)e^{-i(k_x^N x+k_y^M y)} \\ \vdots & \ddots & \vdots \\ C_P(k_x^1, k_y^1)e^{-i(k_x^1 x+k_y^1 y)} & \cdots & C_P(k_x^N, k_y^M)e^{-i(k_x^N x+k_y^M y)} \end{pmatrix} * \begin{pmatrix} R(|k_{11}|) \\ \vdots \\ R(|k_{NM}|) \end{pmatrix}$$

This multi-frequency synthesis technique requires precise mapping of phase and magnitude components of the modulating pattern. One can assume spatial homogeneity with respect to the magnitude of the modulating pattern, so determining the magnitude components is usually straightforward. However, phase mapping can be cumbersome. Since the technique can perform phase mapping, one can apply this to multi-frequency synthesis. In one embodiment, a reflectance standard can be used to generate phase maps of a given pattern, and then use those maps in the Fourier coefficient matrix shown above.

In addition, the Hilbert transform generates an additional, phase-shifted image for each input image. Therefore, using the Hilbert technique in combination with the multi-frequency synthesis technique, it is possible to extract information using multi-frequency synthesis with roughly half the number of frames.

In summary, a limitation with the conventional SFDI demodulation method is that it requires three frames of data for each AC frequency. The developed demodulation technique requires only one image for each AC frequency, reducing SFDI data acquisition time substantially, resulting in faster imaging. The three AC images used in conventional SFDI are phase offset at relative phases of 0, 120, and 240 degrees. This precise mapping of phases for each image requires electronic spatial light modulators such as digital micromirror devices (DMD's). These SLM's have certain disadvantages. For one, they have refresh rates, which can act as a bottleneck with respect with SFDI data acquisition. Also, these devices tend to be expensive, with approximate costs of thousands to tens of thousands of dollars. The developed new demodulation technique does not require precise phase mapping of the modulated light. This allows for new modulation hardware such as static mechanical objects, which are typically less expensive than electronic SLM's.

Example 5

Results

Figure 2:
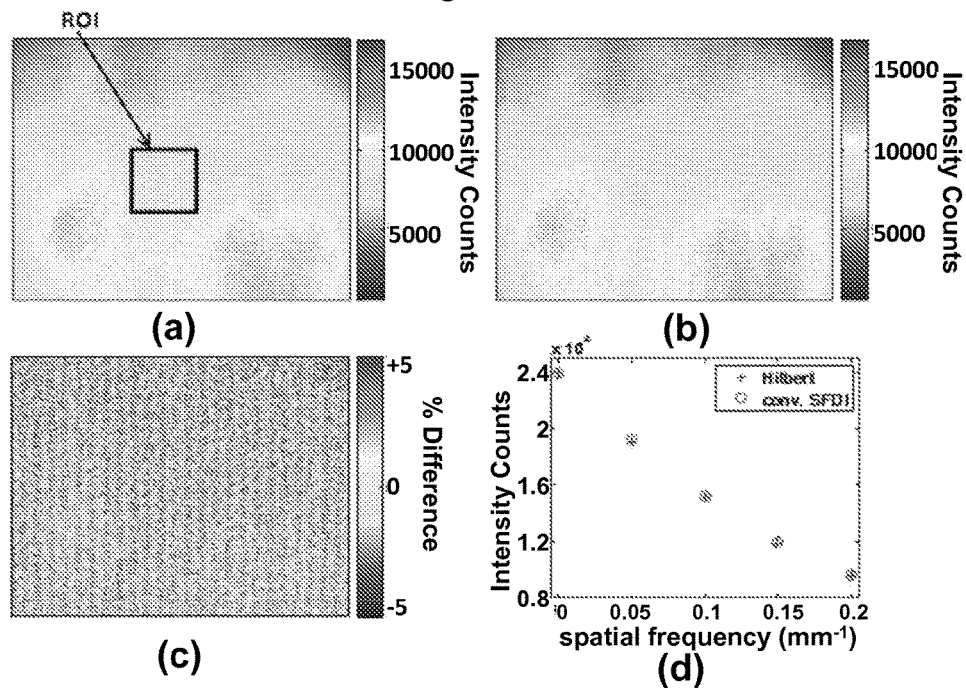
FIG. 2 depicts, in accordance with embodiments herein, demodulated reflectance images of a tissue-simulating phantom using (a) conventional SFDI and (b) using the new Hilbert technique. (c) Map of percent difference in demodulated reflectance between conventional SFDI and the Hilbert technique. (d) Plot of mean diffuse reflectance vs. spatial frequency for the region of interest (shown in a).

To generate the images analyzed in this section, the inventors employed a clinical SFDI system at a wavelength of 658 nm. Optical property values were calculated using a fast look-up table method. FIG. 2 herein shows a comparison between 3-phase SFDI and the Hilbert technique of demodulated, diffuse reflectance maps of a tissue-simulating phantom. Shown are maps of demodulated reflectance for a modulation spatial frequency of 0.2 mm−1. This is the AC spatial frequency that is commonly used in fast, lookup table based SFDI. Here it is seen excellent demodulation quality across the entire field of view, with pixel intensity differences typically well within 5%, with most of the difference being due to the noise contribution from the demodulated images from either technique. There is also shown excellent agreement in diffuse reflectance values between the two techniques, with mean reflectance values within 1% within the region of interest for spatial frequencies ranging from 0 to 0.2 mm−1.

Figure 3:
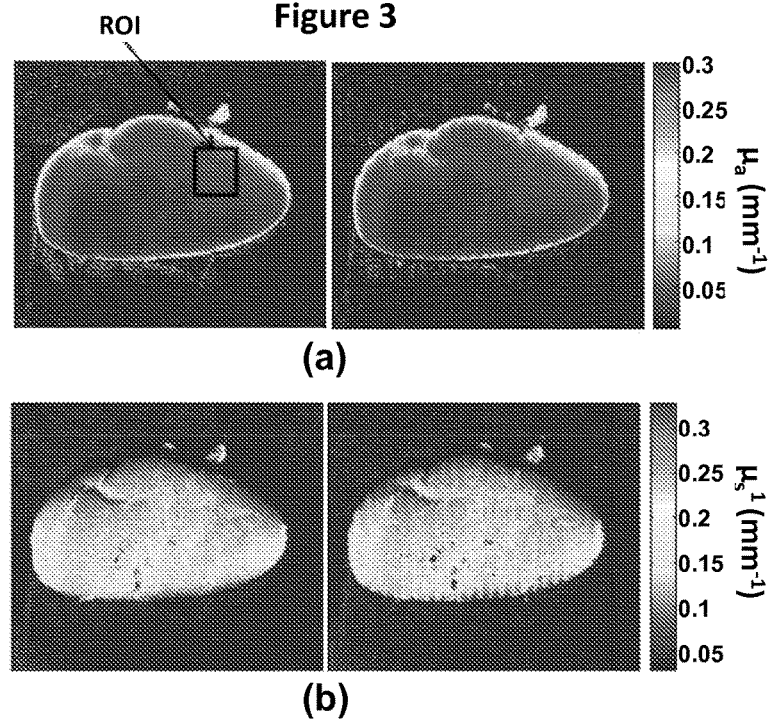
FIG. 3 depicts, in accordance with embodiments herein, in vivo optical property results taken from porcine kidney. (a) Absorption and (b) reduced scattering coefficient maps derived from 4-frame conventional SFDI (left) and the new 2-frame Hilbert technique (right). For both absorption and reduced scattering, the difference in optical property calculations over the region of interest is 0.6%.

FIG. 3 herein shows a comparison between 3-phase SFDI and the Hilbert technique of light absorption and reduced scattering maps of an in vivo porcine kidney sample. Here it is seen excellent agreement in optical property values between the two techniques, with mean absorption and reduced scattering values within 0.6%. The reason why one modulates the light in the first place is to be able to decouple light scattering from absorption in measurements. Therefore, quantitative optical property mapping is an important feature of SFDI. FIG. 3 demonstrates the ability of the developed demodulation technique to produce reflectance maps that lead to accurate optical property calculations in biological tissue.

Figure 4:
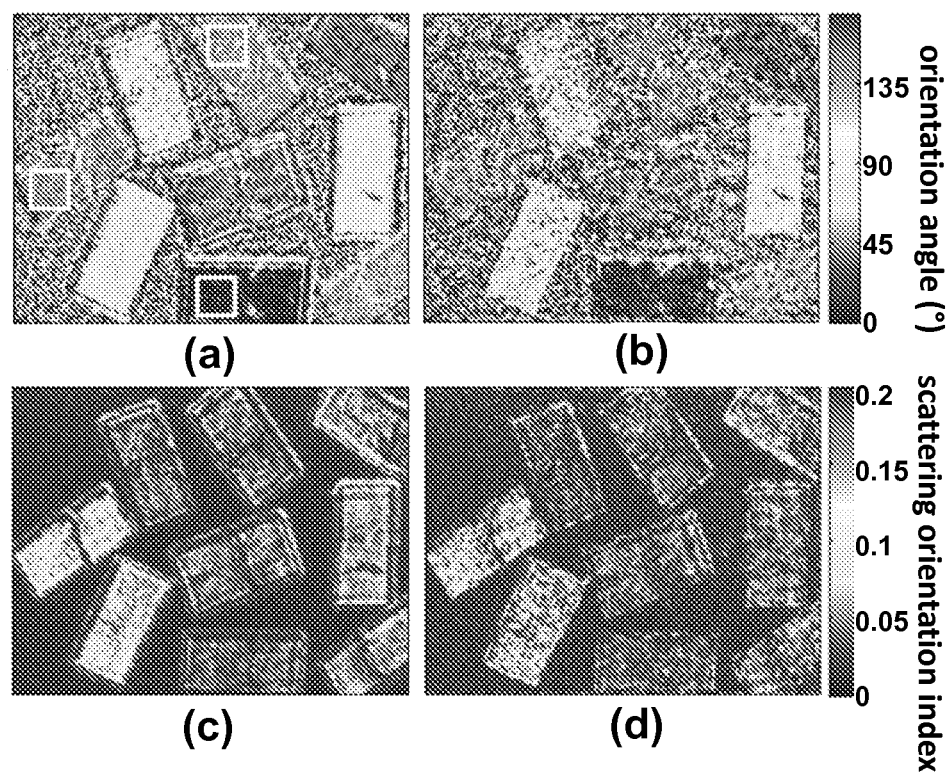
FIG. 4 depicts, in accordance with embodiments herein, scattering orientation results on air filters with known structural anisotropy. Orientation angle maps derived from demodulated reflectance images using (a) 3-phase SFDI and (b) the Hilbert technique. Scattering orientation index (SOI) maps using (c) 3-phase SFDI and (d) the Hilbert technique. Regions of interest (ROI's) were analyzed in 3 filters (white boxes). The difference mean orientation angle determined by the left, top, and bottom ROI's is 0, 1, and 0.75 degrees respectively. The difference in mean scattering orientation contrast (SOI) in the left, top, and bottom ROI's between the Hilbert technique and conventional SFDI is 7.8, 1.7, and 0.27% respectively.

The developed technique has the capability of demodulating rotated sinusoidal patterns. By rotating SFDI modulation patterns, and acquiring diffuse reflectance maps at several angles, one can determine the orientation angle and magnitude of aligned structures in biological tissue. Thus, if one wishes to use the technique to probe tissue orientation, one must verify that it can produce similar contrast as conventional SFDI with respect to orientation. FIG. 4 herein shows scattering orientation and magnitude maps for conventional SFDI and the developed demodulation technique. The orientation angle of the structure being probed is determined by the angle of minimum reflectance. It is seen here that the average orientation angle for all three regions of interest (ROI's) is within 1 degree, which is well within the angular resolution (5 degrees). The mean difference in the scattering orientation index (SOI) for the ROI's is well within 10% for all ROI's, and within 2% for two out of three. This demonstrates an overall good agreement in contrast between results obtained using the developed technique compared to conventional SFDI.

Example 6

Additional Embodiments

Figure 5:
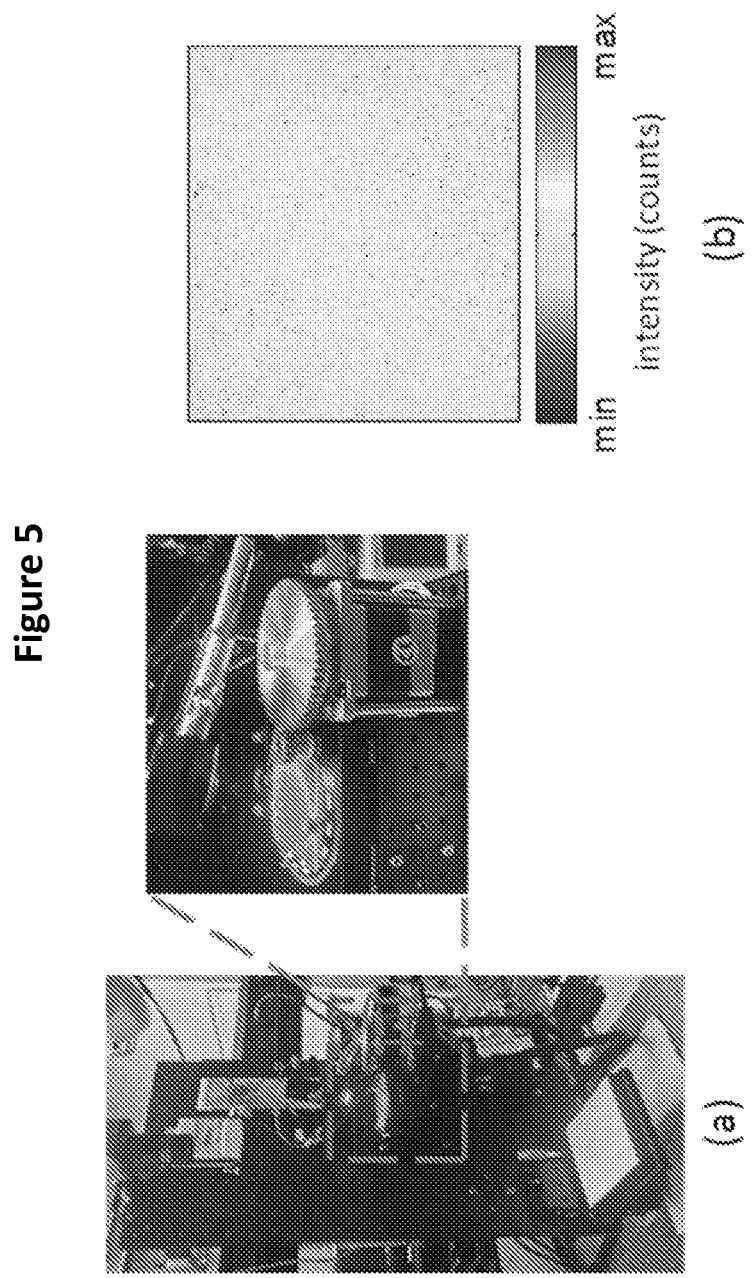
FIG. 5 depicts, in accordance with embodiments herein, (a) Current state of orientation instrumentation using mechanical transmission film coupled to stepper motor for light modulation, and (b) Demodulated AC image of Spectralon reflectance standard using orientation instrument.

Since the developed technique allows for new modulation methods, in one embodiment, the technique may be applied to an instrument that employs a mechanical object for light modulation. In particular, in one embodiment, an instrument geared towards orientation imaging, shown in FIG. 5 herein. This device employs a mechanical transmission film for light modulation. The developed demodulation technique allows one to extract the AC component from modulated images using this system. Since this system is incapable of precise, lateral phase-shifting, the three-phase approach to demodulation cannot be used with this device.

In another embodiment, real-time SFDI and scattering orientation imaging of biological tissue. The developed technique can be integrated into a workflow able to perform SFDI and scattering orientation imaging at near-video or video rate. This should be possible in light of the reduction in data acquisition time by a substantial amount.

Figure 6:
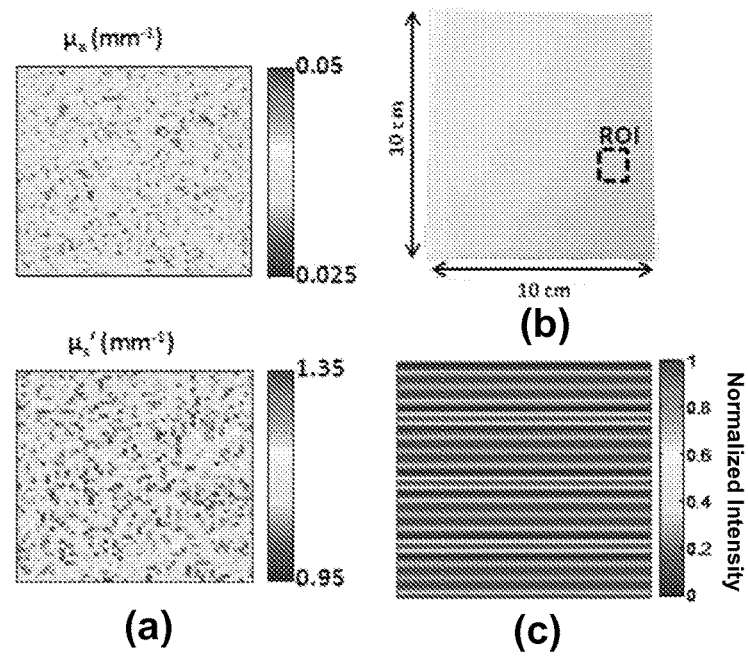
FIG. 6 depicts, in accordance with embodiments herein, results using multi-frequency synthesis standalone. (a) Optical property results obtained using spatial frequency information content derived from applying custom, multi-frequency pattern to tissue-simulating phantom. The difference in mean absorption ($\mu_a$) from the ROI (shown in b) between conventional, 3-phase SFDI and synthesis is 0.00%, while the difference in reduced scattering ($\mu_s'$) was 0.12% (1.1221 vs. 1.1208 mm−1).

In another embodiment, the Hilbert technique may be combined with multi-frequency synthesis. Results using multi-frequency synthesis standalone are shown in FIG. 6 herein. Here, optical property maps of a tissue-simulating phantom were derived by extracting five spatial frequency components from a custom, multi-frequency pattern. A total of nine frames were required to extract the five spatial frequency components.

In accordance with various embodiments herein, using the synthesis technique by itself presents fundamental issues that the Hilbert technique can address. First, a total of two frames are required for each AC frequency contained in the custom pattern. Since the Hilbert technique generates an additional frame of data for each unique frame taken, the number of frames needed for each AC frequency can be reduced to one. Also, the synthesis technique requires accurate spatial phase-mapping of the custom pattern in order to perform the inversion of the center matrix shown in Eq. 7. As shown in Eq. 6, the Hilbert technique can also generate phase maps. Therefore, manual phase-mapping is no longer required (i.e., phase maps can be generated on the fly).

Figure 7:
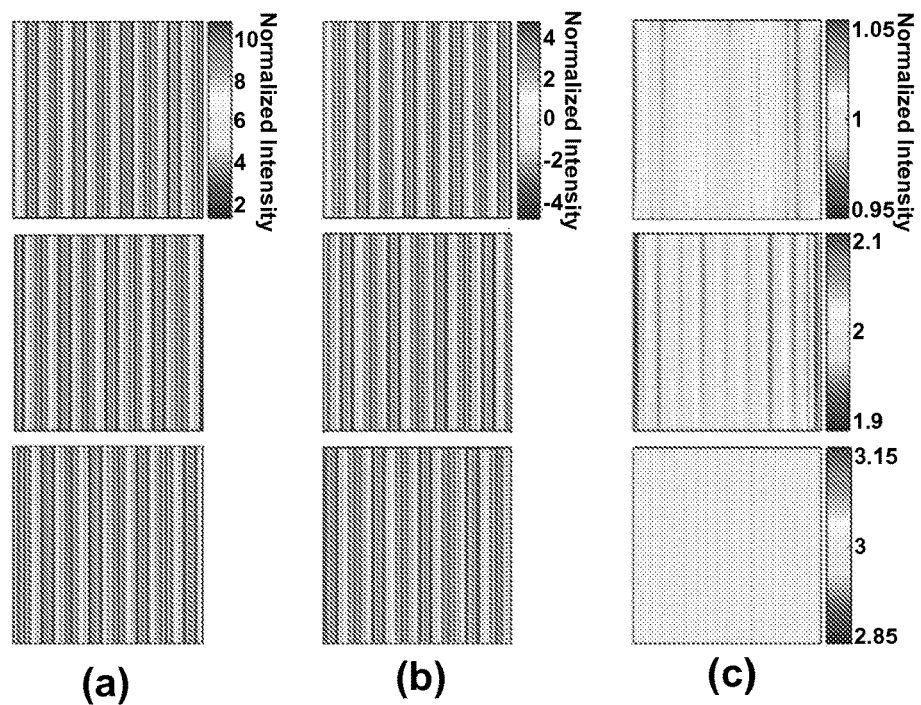
FIG. 7 depicts, in accordance with embodiments herein, simulation data combining the Hilbert and synthesis techniques. (a) Simulated intensity images taken at three phases using a custom, multi-frequency pattern with spatial frequencies of 0, 0.05, 0.15, and 0.25 mm−1 with intensities of 6, 1, 2, and 3 respectively, with a field-of-view of approximately 10×10 cm. (b) Additional, phase-shifted images derived from applying images in (a) to the Hilbert method. (c) Extracted reflectance maps derived from applying images from (a) and (b) to the synthesis technique. The reflectance maps corresponding to 0.05 (top) and 0.15 mm−1 (middle) show reflectance values that are within 2% of the expected value for most pixels, and the map for 0.25 mm (bottom) has reflectance values within 1% of the expected value for most pixels.
Figure 8:
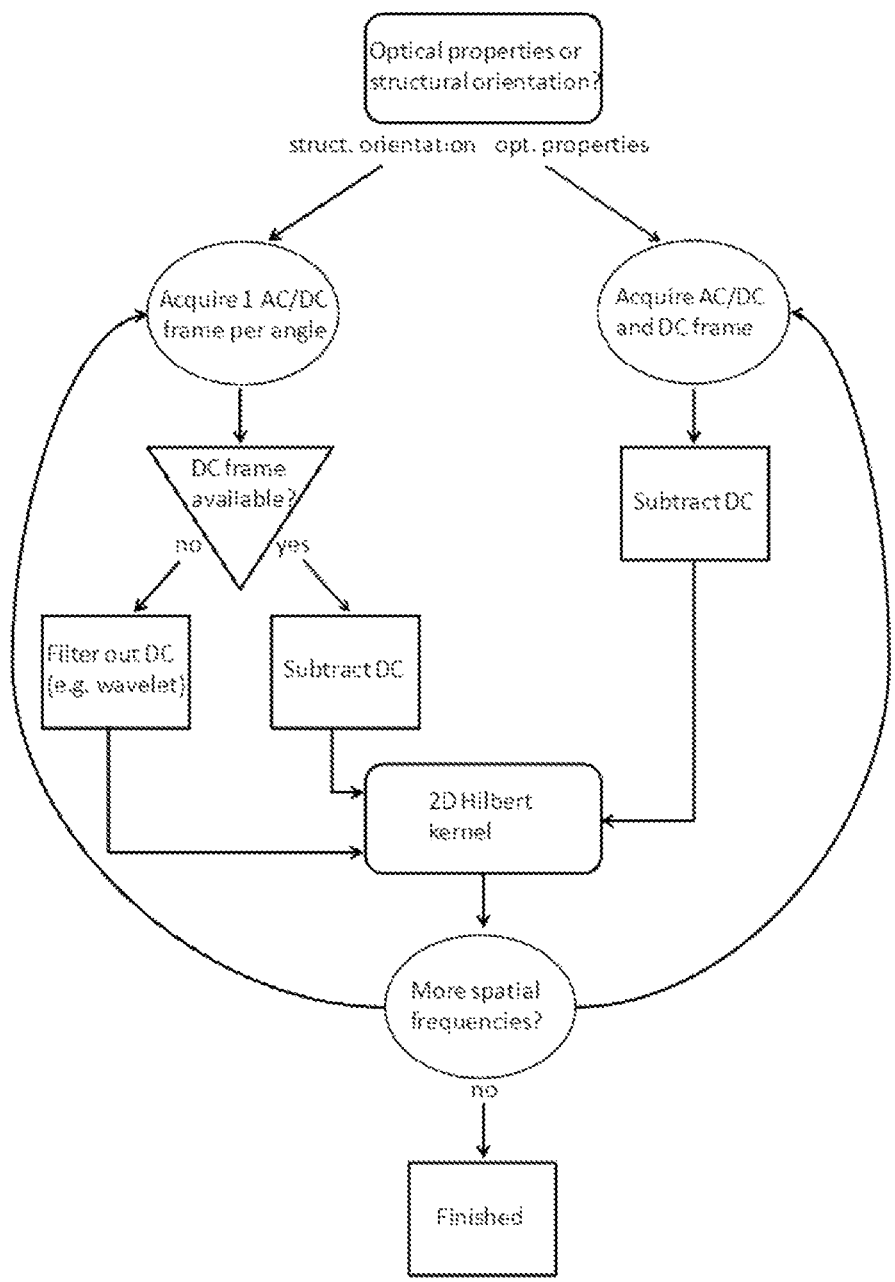
FIG. 8 depicts, in accordance with embodiments herein, a flowchart for data acquisition and processing using the 2D Hilbert technique. This approach allows for the extraction of spatial frequency information for imaging optical properties (absorption and reduced scattering coefficients) and structural orientation contrast.
Figure 9:
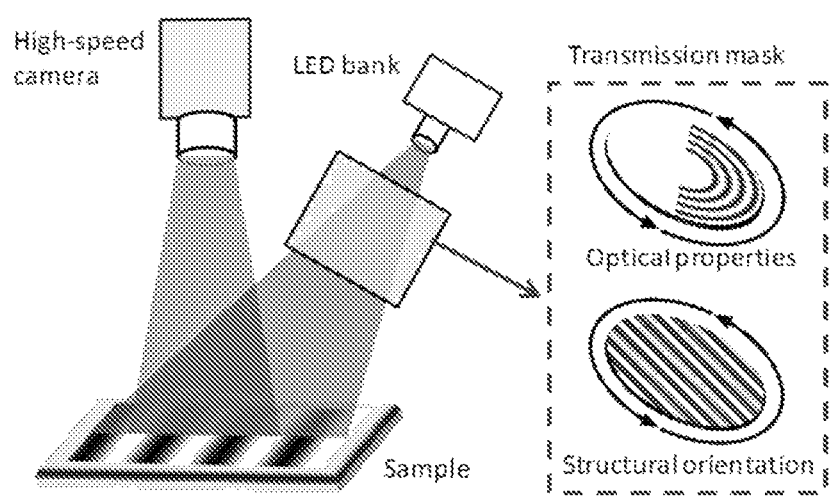
FIG. 9 depicts, in accordance with embodiments herein, SFDI instrument using a printed film spatial light modulator (SLM). The SLM can be powered through an electric motor, and hall sensors on the motor can be synced with the camera and light source for triggering. When the SLM reaches a desired position (i.e. one half rotation for optical properties or orientation angle for structural orientation) a pulse is sent from the motor to the camera and LED bank to snap a frame and switch wavelengths, respectively, allowing for a completely hardware-triggered system.
Figure 10:
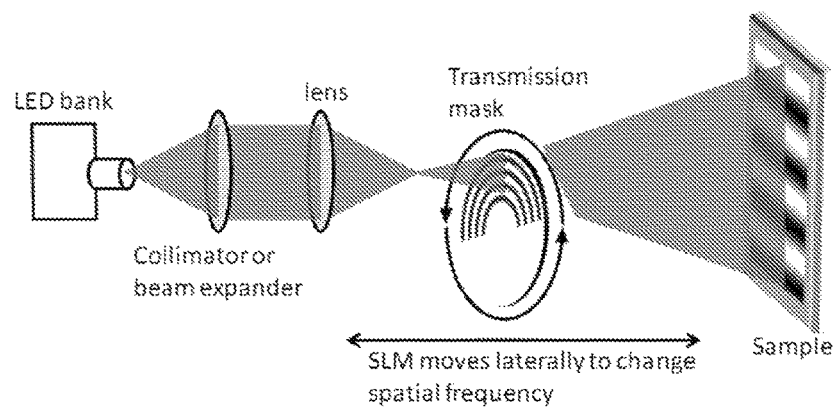
FIG. 10 depicts, in accordance with embodiments herein, a schematic of light path for rapid, multi-frequency acquisition. Light from an LED (or laser) source passes through a collimator or beam expander. A positive lens images light onto printed film SLM. The SLM is attached to a lateral stage, which moves the SLM back and forth. Consequently, the spatial frequency of the pattern impinging the sample is changed. When the SLM is closer to the positive lens, the image is smaller, and thus the projected pattern has a lower spatial frequency. Conversely, when the SLM is further away, the image is larger, and the projected pattern has a higher spatial frequency. The DC half of the SLM is unaffected by the lateral movement of the SLM.
Figure 11:
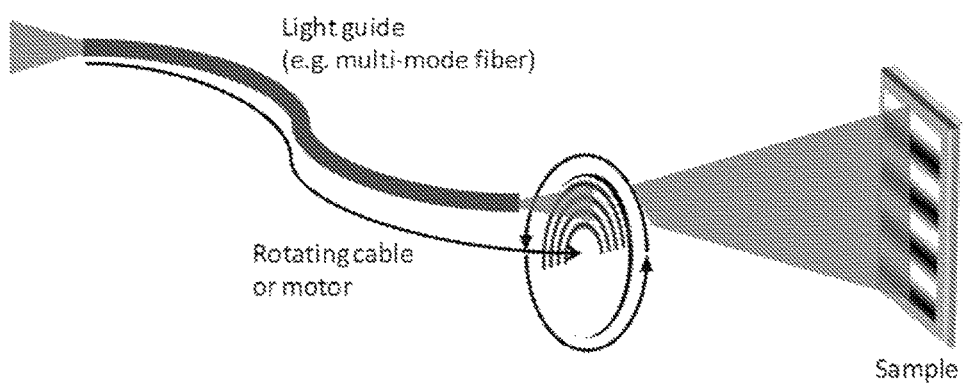
FIG. 11 depicts, in accordance with embodiments herein, a schematic of an endoscope embodiment using custom printed film SLM. Light is passed through a waveguide (e.g. multimode fiber). The light output from the waveguide passes through a rotating SLM. The camera can be rotated by a cable coupled to a rotary joint, or a small motor at the end of the endoscope.

In accordance with various embodiments herein, simulation data combining the Hilbert and synthesis techniques is shown in FIG. 7 herein. The custom pattern used here is based on the Fourier series of a square wave. In particular, the first three terms in the series were used, with spatial frequencies of 0.05, 0.15, and 0.25 mm−1. Spatial frequencies in this range have been used previously to perform tomographic reconstruction in the spatial frequency domain.

In another embodiment, combing the synthesis and Hilbert techniques allow performance of tomography in the spatial frequency domain using a mechanical object having a single, multi-frequency pattern. In addition, the concept of tomography can be extended to tissue orientation, by rotating the multi-frequency pattern to obtain several frames of data. This will allow one to probe tissue orientation as a function of depth.

Example 7

Optical Properties

If optical properties are desired, a DC (planar illumination) and DC-offset, AC image (structured light) is acquired. The "switching" mechanism between DC and AC/DC projection patterns can be accomplished in a number of ways, including, but not limited to:
  Electronic spatial light modulator (such as DMD), toggling between planar and structured patterns
  Rotating disc with printed DC and sinusoidal patterns (½ DC, ½ sinusoidal)
    Pattern fringes can be curved or angled, since Hilbert technique is insensitive to pattern orientation
    Phase angle of pattern is arbitrary; peaks and valleys of pattern can be placed anywhere in the field-of-view
    This type of modulator can operate in reflection or transmission geometry, and could be integrated into endoscope form factor
  Linear translation stage with printed DC/sinusoidal patterns Next, the DC component is subtracted from the DC-offset, AC image, isolating the AC component. This AC image is applied to the 2D Hilbert transform kernel, which demodulates the AC frequency component in the image, upon which information is embedded, and is used to compute images of optical properties.

The minimum number of spatial frequency components required to derive optical properties is 2 (e.g. DC and a single AC frequency). However, multiple spatial frequency components can be used to perform depth localization and/or improve optical property fitting. To enable rapid switching between spatial frequencies, the printed mask or a lens could be moved via a linear translation stage.

Example 8

Structural Orientation Contrast

If structural orientation contrast is desired, multiple AC/DC images (1 for each orientation angle) are acquired. The "switching" mechanism between the multiple AC projection angles can be accomplished in a number of ways, including, but not limited to:
  Electronic spatial light modulator (such as DMD), projecting the different angles Rotating disc with printed sinusoidal pattern (oriented straight across field of view)
Phase angle of pattern is arbitrary; peaks and valleys of pattern can be placed anywhere in the field-of-view
This type of modulator can operate in reflection or transmission geometry, and could be integrated into endoscope form factor If the instrument is unable to provide a DC image (i.e. rotating sinusoid pattern), the DC component from the AC/DC frames can be removed using signal processing techniques such as a 2D wavelet filter. Otherwise, the DC is simply subtracted using a dedicated DC frame. Next, each AC frame is applied to the 2D Hilbert algorithm.

Similarly to optical properties, the spatial frequency can be rapidly switched using a translation stage setup.

Example 9

Demodulation Technique—Overview

As disclosed herein, the inventors have developed a method for extracting spatial frequency information content from biological tissue, which in one embodiment, may be used to calculate tissue optical properties and determine tissue structural orientation. This demodulation method employs a 2D Hilbert transform using a spiral phase function in Fourier space. In another embodiment, the approach allows for the determination of tissue optical properties using a single frame of data for each modulation frequency, increasing imaging speed by two-to-threefold versus conventional, 3-phase spatial frequency domain imaging (SFDI). In another embodiment, the single-phase Hilbert transform approach recovers optical property and scattering orientation index (SOI) values within 1% and 10% of 3-phase SFDI, respectively. These results demonstrate that using the Hilbert demodulation technique, SFDI data acquisition speed can be increased significantly while preserving data quality, which allow the implementation of a real-time SFDI platform.

Example 10

Figure 12:
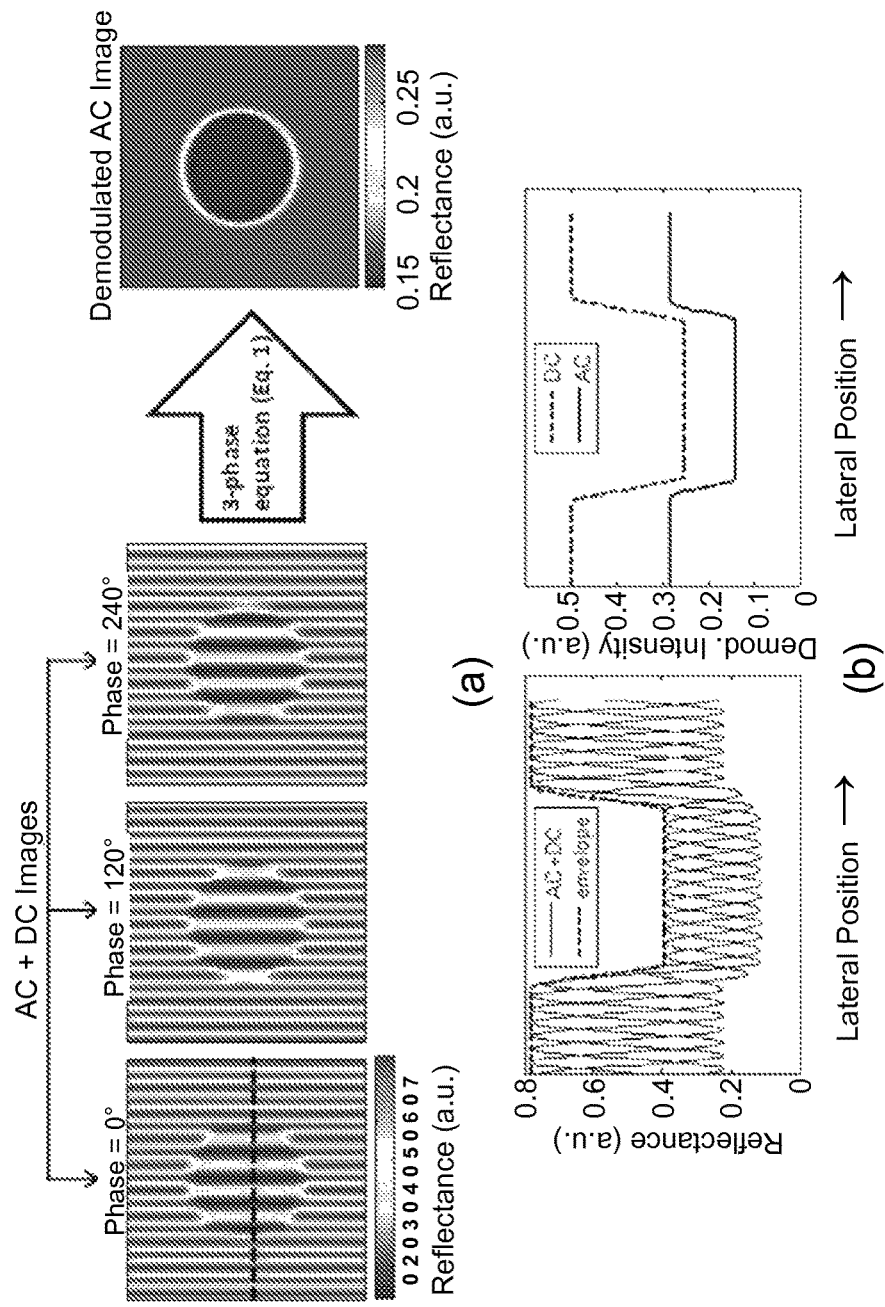
FIG. 12 depicts, in accordance with embodiments herein, a demodulation technique. (a) Simulation of 3-phase demodulation technique on a turbid sample with uniform scattering and a circular absorbing lesion in the center of the field of view. Images are acquired at relative modulation phases of 0, 120, and 240 degrees. These images are then applied to a 3-phase demodulation formula (Eq. 1), which extracts the AC information content from the sample pixel-by-pixel. (b) Plot of reflectance cross-sections taken from the center row (dashed line shown in a) of each AC+DC image, and the resulting AC+DC information envelope (left). Also shown is a cross-section of the demodulated DC (taken from additional planar image) and AC information content (right). The DC cross-section is more sensitive than AC to absorption, while the AC cross-section is more sensitive than DC to scattering.

Demodulation Technique—Materials and Methods
Spatial Frequency Domain Imaging (SFDI):

Structured light is projected onto a sample using a spatial light modulator (SLM), and a camera detects the diffusely reflected light emitted from the boundary of the sample. In 3-phase SFDI, three frames of data are acquired at relative modulation phases of 0, 120, and 240 degrees for each AC spatial frequency. These phase-offset images are applied to a simple formula to extract the AC information content pixel-by-pixel, shown in Eq. 1. A simulation of this demodulation approach using three phase-offset modulation patterns is shown in FIG. 12 herein. All data processing and computation used to produce figures was performed using the MATLAB software suite (MATLAB and Statistics Toolbox Release 2011b, The MathWorks, Inc., Natick, Mass.).

$$AC(x, y) = \frac{2^{1/2}}{3}\{[I_{0°}(x, y) - I_{120°}(x, y)]^2 + [I_{120°}(x, y) - I_{240°}(x, y)]^2 + [I_{240°}(x, y) - I_{0°}(x, y)]^2\}^{1/2} \quad (1)$$

Next, the demodulated intensity data from the sample is calibrated to that of a tissue-simulating phantom having known optical properties. This calibrated diffuse reflectance data at each spatial frequency is then applied to a light transport model such as diffusion or Monte Carlo, from which $\mu_a$ and $\mu_s'$ maps are determined. Finally, these maps are generated at several wavelengths, and are fit to known chromophore spectra to quantitatively determine the concentration of relevant chromophores in the sample.

In order to decouple scattering from absorption, at least two spatial frequencies are required. In the case where the minimal number of frames are taken, 0 mm$^{-1}$ (planar illumination) and 0.2 mm$^{-1}$ are typically used. Since there is no spatial variation in the modulation pattern at 0 mm$^{-1}$, only one phase is required, so a minimum of four frames total are needed in 3-phase SFDI, consisting of a single DC frame, and three phase-offset, AC frames. After demodulation, a fast lookup table is employed to determine $\mu_a$ and $\mu_s'$. The primary limitation with respect to the implementation of real-time SFDI is data acquisition time. In particular, as they practice the technique, the need to acquire three frames of data for each AC spatial frequency limits the speed of SFDI data acquisition. The inventors have developed a technique to address this bottleneck, by reducing the number of frames required for each modulating frequency from three to one.

2D Hilbert Demodulation Technique:

The Hilbert transform is a ubiquitous tool in signal processing, with a wide variety of applications in the communication field. The general principle is that a modulating double-sideband signal such as a sine or cosine contains redundant information; only one sideband is needed to extract the modulated information content. Using the Hilbert transform, one can derive a single-sideband expression for this modulated signal with no loss of information. This single-sideband expression allows for the extraction of the demodulated information content and phase map of the modulated signal. The concept of applying the Hilbert transform using spiral phase functions in 2D Fourier space to demodulate 2D curved patterns in space can be adopted and then applied to the SFDI workflow.

The modulated reflectance images obtained in SFDI can be described by Eq. 2 and Eq. 3, where $f_{x,y}$ is the modulating spatial frequency, and $\emptyset_{x,y}$ is the phase.

$$I(x,y)=0.5*R_{DC}(x,y)+0.5*M(x,y) \quad (2)$$

Where $$M(x,y)=R_{AC}(x,y)*\cos\{2\pi f_{x,y}+\emptyset_{x,y}\} \quad (3)$$

The purpose of demodulation is to extract the AC diffuse reflectance term $R_{AC}(x, y)$ from the detected amplitude $I(x, y)$. Using Euler's theorem, a cosine function can be expressed as the sum of two complex exponentials, or sidebands in the frequency domain. As mentioned previously, the Hilbert transform is used to obtain a single-sideband expression for a double side-band function such as a cosine. Since a single-sideband function can be expressed as a complex exponential, demodulation is straightforward. The magnitude of the single side-band expression for SFDI modulation results in the diffuse reflectance we wish to obtain.

The inventors' SFDI demodulation approach employs a 2D Hilbert transform to SFDI frames by applying a spiral phase function to the image in 2D Fourier space. One unique aspect of this approach is that it can demodulate frames whose modulation patterns are rotated, or arbitrarily oriented. That is, the wavenumber of the modulating pattern can have arbitrary directionality with respect to the lateral imaging axes (x,y). The spiral function is described in Eq. 4.

$$S(u, v) = \frac{u + iv}{\sqrt{u^2 + v^2}} \quad (4)$$

Where u and v are the lateral coordinates in 2D Fourier space.

In order to implement the Hilbert demodulation technique, the following steps are performed. First, the DC component of the modulated image, which consists of both AC and DC components (I(x, y) from Eq. 2), is removed. A 2D FFT is then applied to the resulting AC image (M(x, y) from Eq. 2). In 2D Fourier space, the transformed AC image is multiplied by a map generated using Eq. 4, having the same dimensions as the AC image. Next, an inverse FFT is applied to this product. The resulting image is similar to the original AC image, except that the modulating "cosine" is now a "sine", i.e. the phase of the modulating wave is shifted by 90 degrees. Then the magnitude of this "sine" image is taken, which accounts for the complex contribution of the transformed map due to the orientation angle of the modulating wave, shown in Eq. 4. The resulting term, H(x,y), represents the Hilbert transform of the original AC image (M(x, y)). Finally, H(x, y) is multiplied by the complex unit and added to the AC component of the original AC image. The resulting magnitude is the demodulated AC diffuse reflectance, denoted in Eq. 5 by R(x, y).

$$R(x,y)=|M(x,y)+iH(x,y)| \quad (5)$$

Where $$H(x,y)=|FFT^{-1}\{FFT(M(u,v))*S(u,v)\}| \quad (6)$$

A walkthrough of the Hilbert technique is shown in FIG. 2 using a simulated DC and AC+DC image. In this simulation the sample is highly reflective, such that the sinusoidal pattern is kept intact as the light reaches the boundary of the sample. In reality we apply this technique to turbid samples, which will be demonstrated in the experimental results, but this virtual sample was chosen to clearly illustrate the Hilbert demodulation concept. The Hilbert technique will yield results comparable in quality to those shown in FIG. 13 herein, so long as the reflected modulation pattern is higher in amplitude than the camera noise, which is typically the case when looking at biological samples.

Here one can begin with a DC image at a uniform intensity of one, and an AC+DC image (Eq. 2) with an intensity varying from zero to one, with a modulation pattern oriented diagonally. First, the DC component is removed from the AC+DC image, and an FFT is performed on the resulting AC image. Next, the spatial frequency map of the transformed AC image is multiplied with the complex spiral function map. The resulting map is then FFT inverted, and the magnitude is taken. This "magnitude" image is then multiplied by the imaginary unit, and added to the initial AC image (before Hilbert transform). The magnitude of this sum results in the demodulated AC diffuse reflectance, which is uniform at an intensity of approximately 0.5.

It should be noted that the demodulated AC images obtained in FIG. 12 herein and subsequent figures using the Hilbert technique contain residual ringing artifacts. These are due to the fact that the sinusoidal patterns are cutoff by the boundaries of the image, and are therefore finite in length. Although these artifacts are generally minor, they increase in severity as the number of periods in the modulation pattern in the image decreases. Therefore, one strategy to minimizing these artifacts, particularly at lower spatial frequencies, is to use an SFDI instrument having a large field of view. Alternatively, a window function such as a Gaussian or Hamming filter could be applied to the image in post-processing to mitigate these artifacts.

The inventors performed a side-by-side comparison of our advanced Hilbert demodulation technique to 3-phase demodulation. To generate the data used to produce the images analyzed in this section, we employed a clinical SFDI system at a wavelength of 658 nm. In the first experiment, the inventors compared diffuse reflectance maps obtained on a tissue-simulation phantom at multiple spatial frequencies. This phantom consists of a silicone foundation consisting of India ink as an absorbing agent, and titanium dioxide as the scattering agent. Next, they compared $\mu_a$ and $\mu_s'$ maps extracted from an in vivo human forearm. Finally, they evaluated SOI maps taken on a structural orientation phantom consisting of a silicone-based bottom layer (described above), and a top layer composed of sections of pleated air filters at various orientation angles.

Example 11

Demodulation Technique—Results

Figure 14:
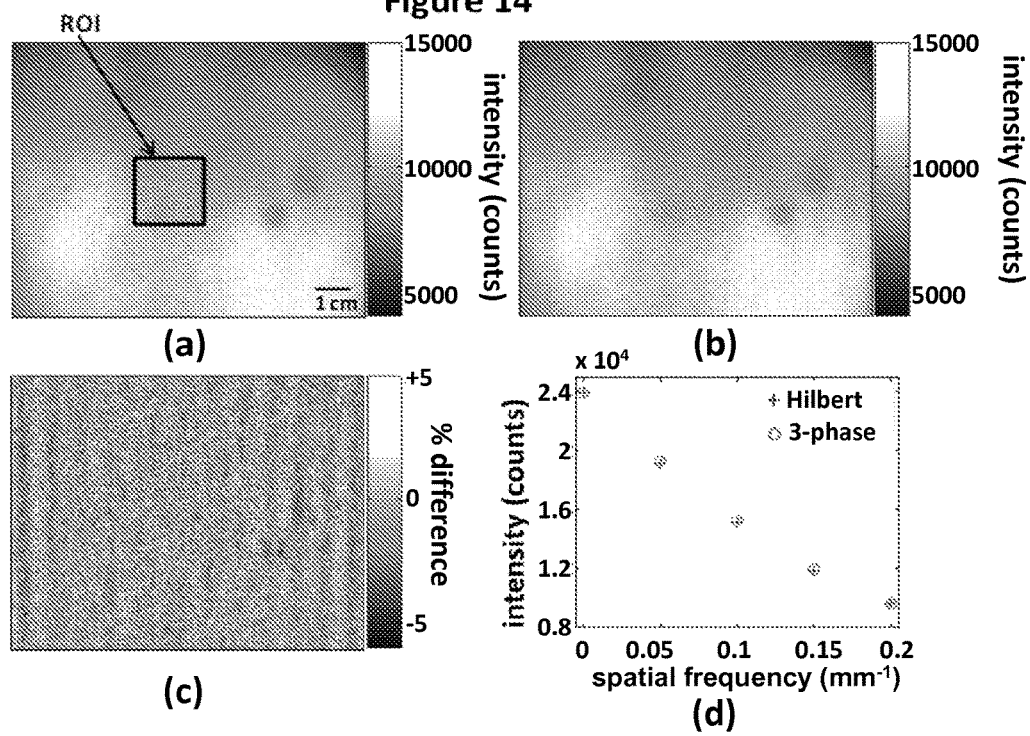

Tissue Phantom Reflectance Experiment:

Demodulation in the SFDI workflow allows for the extraction of information content in the SFD, which is used to generate $\mu_a$ and $\mu_s'$ maps. FIG. 14 herein shows a comparison between 3-phase SFDI and the Hilbert technique of demodulated, diffuse reflectance maps of a homogeneous tissue-simulating phantom. Shown are maps of demodulated reflectance at an AC spatial frequency of 0.2 mm$^{-1}$. Here, only the first phase)(0° intensity image is applied to the Hilbert technique, while intensity images at three phases (0°, 120°, 240°) are applied to 3-phase demodulation (shown in Eq. 1). Also shown are average demodulated diffuse reflectance results at five spatial frequencies evenly distributed from 0-0.2mm$^{-1}$ taken from the region of interest (ROI) shown in the black box. These spatial frequencies are typically employed in the SFDI workflow, and instrumentation and models have been shown to perform adequately in this range. Here one sees good demodulation quality across the entire field of view, with pixel intensity differences between 3-phase and Hilbert generally within 5%. It is also shown agreement in diffuse reflectance values between the two techniques, with mean reflectance values within 1% within the ROI for spatial frequencies of 0.05, 0.1, 0.15, and 0.2 mm$^{-1}$. It should be noted that, although the sample in this case is homogeneous, the reflectance intensity over the field of view is not. This is due to the inhomogeneity of the light source, which is accounted for during calibration.

Accurate demodulation, and thus determination of AC information content in the SFD, is a necessary component of SFDI, and is what allows for the generation of $\mu_a$ and $\mu_s'$ maps. In the following section, presented are $\mu_a$ and $\mu_s'$ maps extracted from a volar forearm using the Hilbert demodulation technique, and compare this data directly to $\mu_a$ and $\mu_s'$ maps derived using 3-phase demodulation.

Figure 15:
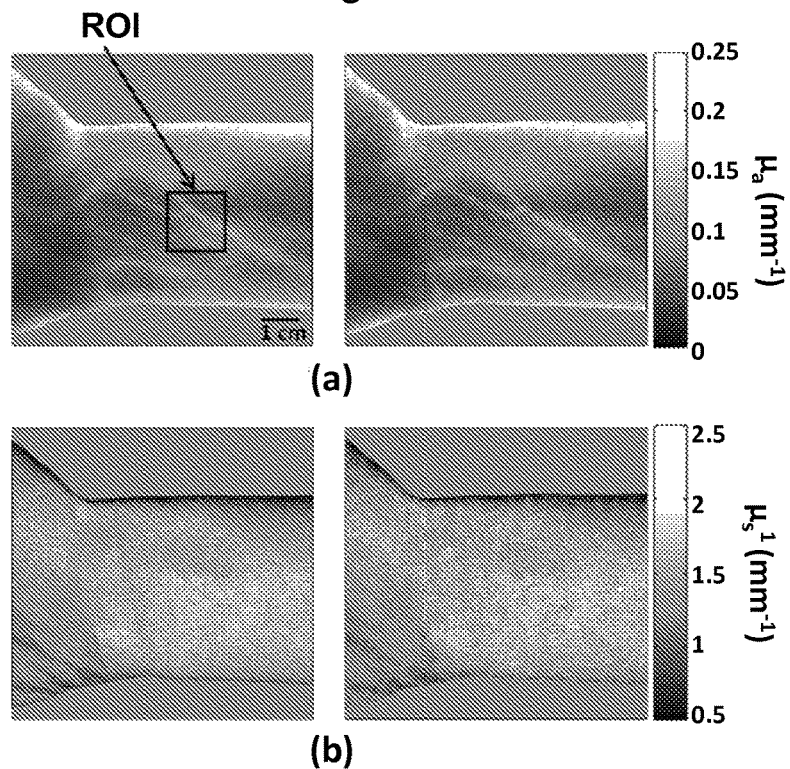
FIG. 15 depicts, in accordance with embodiments herein, in vivo optical property results taken from a human volar forearm. (a) Absorption ($\mu_a$) and (b) reduced scattering ($\mu_s'$) coefficient maps derived from 4-frame, 3-phase SFDI (left) and the 2-frame, Hilbert (right) demodulation techniques. For $\mu_a$ and $\mu_s'$, the difference in optical property calculations over the region of interest (ROI, shown in black box) is 0.2% and 0.15%, respectively.

In Vivo Volar Forearm Experiment:

Optical property maps of a human volar forearm were calculated using a fast lookup table method, employing spatial frequencies of 0 and 0.2 mm$^{-1}$. FIG. 15 herein shows a comparison of $\mu_a$ and $\mu_s'$ maps of the forearm using the 3-phase (left column) and Hilbert (right column) demodulation techniques. Here one can see agreement in optical property values between the two techniques, with the difference in mean $\mu_a$ and $\mu_s'$ values in the ROI (shown in the black box) being 0.2% and 0.15%, respectively.

A key motivation for spatially modulating light in SFDI is to decouple scattering from absorption. Therefore, quantitative optical property mapping is an essential feature of the technique. FIG. 15 herein demonstrates the ability of the new demodulation technique to produce $\mu_a$ and $\mu_s'$ maps in biological tissue that agree with the conventional demodulation method, which suggests that we can reduce this new technique to practice. The payoff using the new Hilbert technique is the reduction in frames of data required to derive $\mu_a$ and $\mu_s'$, and thus an increase in data acquisition speed. In the case shown in FIG. 15 herein, the number of frames reduced using the Hilbert technique over 3-phase demodulation is from four to two, resulting in a twofold increase in imaging speed. However, the payoff in speed increases further if more spatial frequencies are employed, asymptotically approaching a threefold increase.

Figure 13:
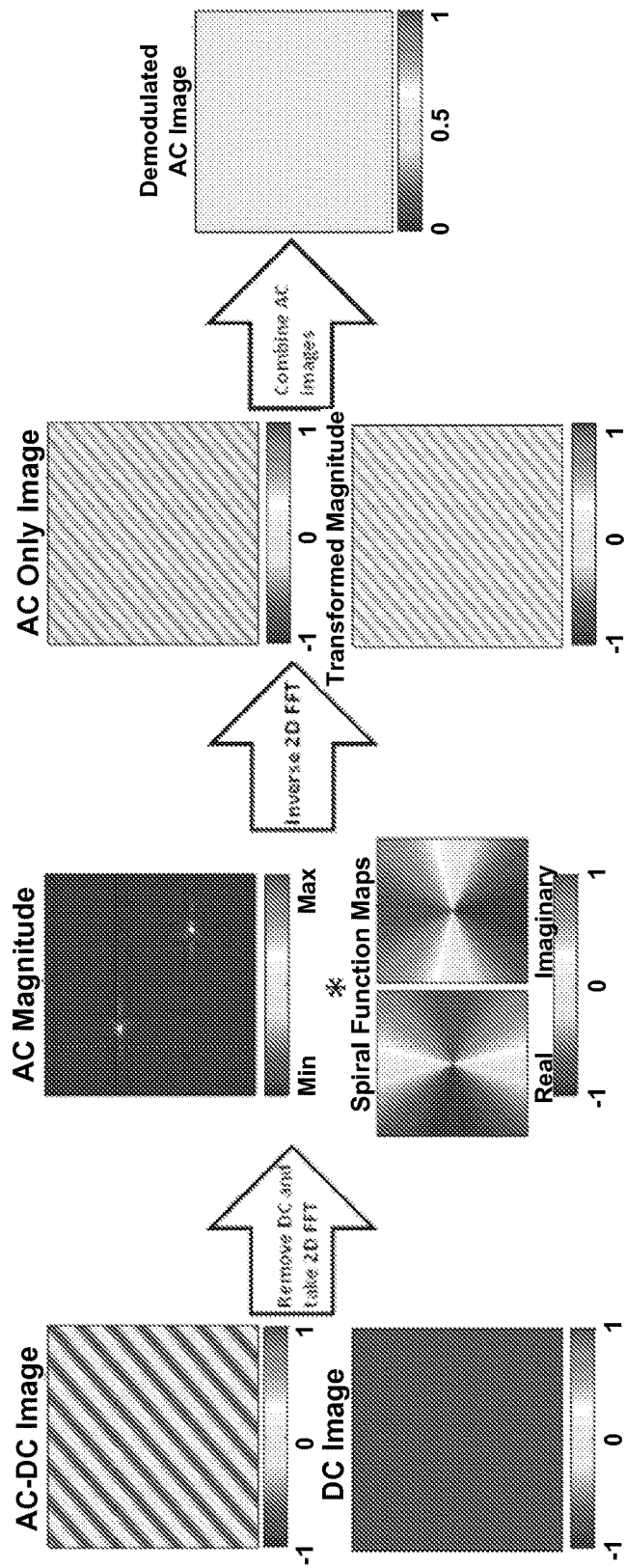
FIG. 13 depicts, in accordance with embodiments herein, a simulation of the 2D Hilbert demodulation method on a highly reflecting surface. First, the DC component of the modulated image is removed, and a fast Fourier transform (FFT) is performed on the AC+DC image. The resulting 2D map in Fourier space is then multiplied by a spiral phase function, consisting of a continuous, radially-varying map ranging in value from −1 to +1 in real and imaginary space. An inverse FFT is performed on the map, resulting in an image whose magnitude is the original modulated image phase-shifted by 90 degrees. This image is multiplied by the imaginary unit and added to the original image. The magnitude of this image results in the demodulated diffuse reflectance of the AC component from the original AC+DC image.

Although the primary benefit of using the Hilbert technique over 3-phase demodulation is the increase in imaging speed, there are additional benefits. In particular, as shown in FIG. 13, the Hilbert technique can demodulate rotated, or oriented sinusoidal patterns using only one AC phase. Acquiring reflectance data at multiple sinusoidal pattern orientation angles is used to characterize tissue structural orientation in the SFD. The following section shows orientation angle and contrast maps on tissue structural orientation phantoms using both the Hilbert and 3-phase demodulation techniques.

Figure 16:
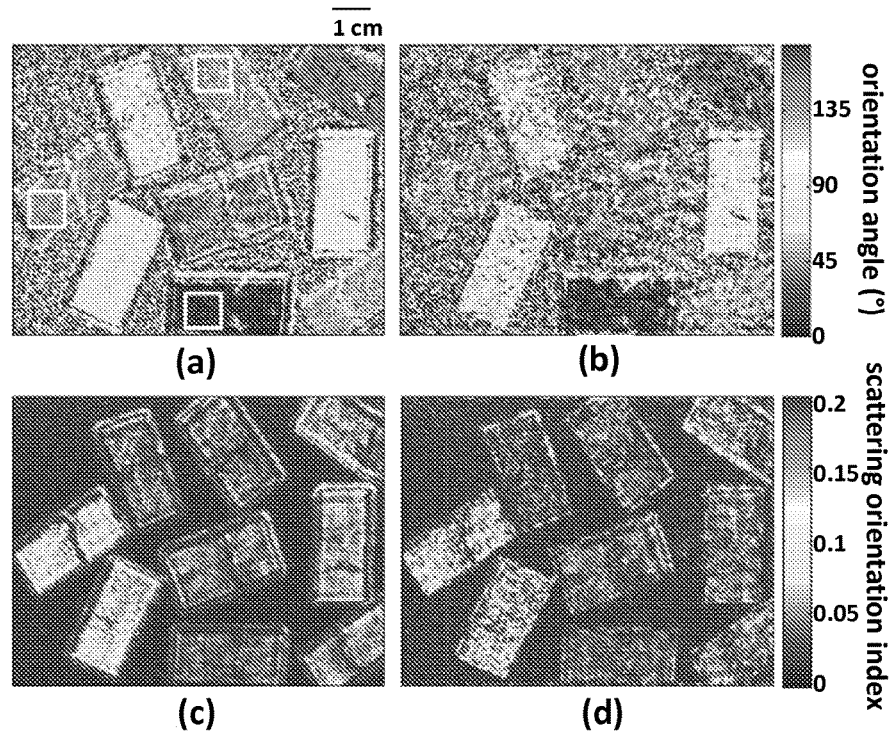
FIG. 16 depicts, in accordance with embodiments herein, structural orientation results on structural orientation phantoms consisting of air filters with known structural anisotropy. Orientation angle maps derived from demodulated reflectance images using the (a) 3-phase and (b) the Hilbert technique. Scattering orientation index (SOI) maps using (c) 3-phase SFDI and (d) the Hilbert technique. Regions of interest (ROI's) were analyzed in 3 filters (white boxes). The difference mean orientation angle determined by the left, top, and bottom ROI's is 0, 1, and 0.75 degrees respectively. The difference in mean scattering orientation contrast (SOI) in the left, top, and bottom ROI's between the Hilbert technique and conventional SFDI is 7.8, 1.7, and 0.27% respectively.
Figure 17:
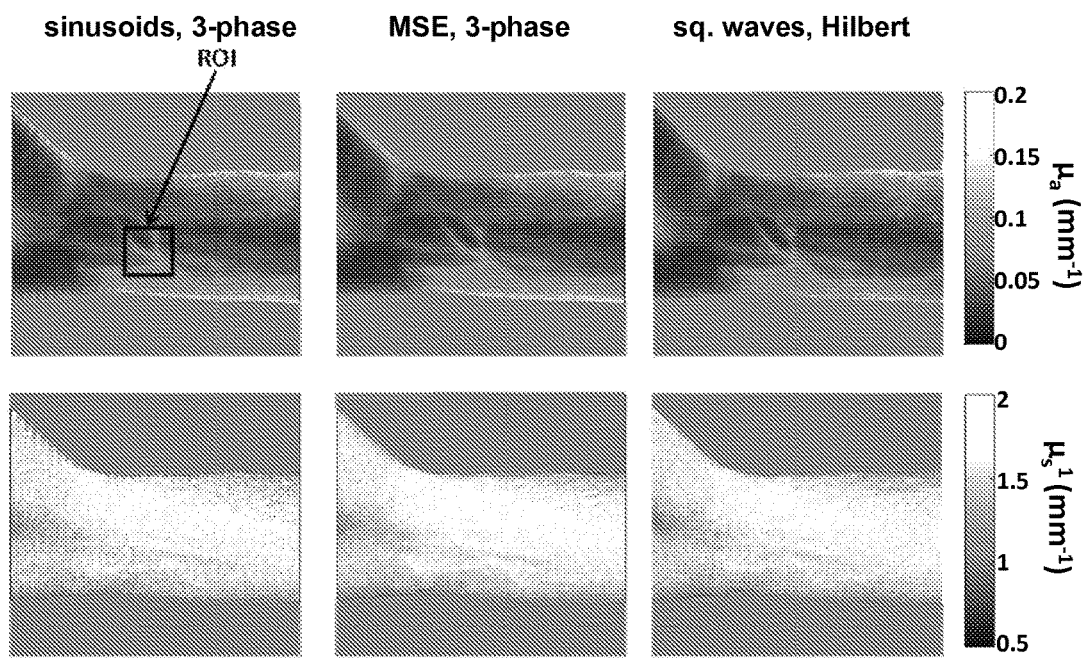
FIG. 17 depicts, in accordance with embodiments herein, in vivo human forearm optical property results obtained using sinusoidal patterns and the 3-phase demodulation equation (gold standard, left column), multi-frequency synthesis and extraction (MSE) and square waves (middle column), and the Hilbert demodulation technique and a single square wave and planar image (right) column. For each case, optical property results generally agree to within 1%. MSE requires 3 frames of data, while Hilbert requires 2, resulting in a ⅓ reduction in data acquisition time.

Scattering Orientation Experiment:

By rotating SFDI modulation patterns and acquiring diffuse reflectance maps at several projection angles, one can determine the orientation angle and magnitude of structures in biological tissue. Therefore, if one wishes to use the Hilbert technique to probe tissue orientation, one must verify that it can produce similar structural orientation contrast as 3-phase SFDI. FIG. 16 shows scattering orientation angle and contrast maps for the 3-phase and Hilbert techniques at an AC spatial frequency of 0.2 mm$^{-1}$. The orientation angle of the structure being probed is determined by the angle at which minimum diffuse reflectance is detected. One can see herein that the average orientation angle for all three ROI's (shown in white boxes) is within 1 degree, which is well within the angular resolution of 5 degrees.

To assess the degree to which the underlying structures are oriented, they used a normalized quantity known as the scattering orientation index (SOI), shown in Eq. 7 [11]. Here, the SOI is determined by maximizing, for all projection angles, the reflectance taken at a given angle subtracted by the reflectance taken at the orthogonal projection angle, divided by the sum. The tissue structure orientation phantoms used consist of rectangular-shaped, pleated air filters having significant structural orientation, placed on top of a tissue-simulating phantom having minimal structural orientation.

$$SOI = \max\left\{\frac{|g(\theta)| - |g(\theta + \pi/2)|}{|g(\theta)| + |g(\theta + \pi/2)|}\right\} \quad (7)$$

FIG. 16 herein shows SOI maps of tissue structural orientation phantoms using the 3-phase (left column) and Hilbert (right column) demodulation techniques. In general, the SOI values obtained using the Hilbert technique are within 10% of those obtained using 3-phase demodulation.

In particular, the mean difference in the SOI is well within 10% for the three ROI's, and within 2% for two out of three of the ROI's. This demonstrates an overall agreement in SOI between results obtained using the Hilbert and 3-phase techniques.

Since the characterization of structural orientation in SFDI uses multiple projection angles of sinusoidal patterns, several frames of data are required. In the case shown in FIG. 16, the angular resolution in orientation analysis is five degrees. Since the orientation angle has a range of 0-180 degrees, 36 projection angles were employed. Using the 3-phase technique, this results in a total of 108 frames, while the Hilbert technique requires only 36 frames (one frame per projection angle). Thus, the Hilbert technique in this example increases imaging speed threefold over 3-phase demodulation.

Presented in accordance with various embodiments herein, the inventors have created a method for extracting spatial frequency information content from biological tissue, which employs a 2D Hilbert transform using a spiral phase function in 2D Fourier space. This demodulation technique increases SFDI optical property data acquisition speed by two-to-threefold over conventional, 3-phase demodulation, depending on the number of spatial frequencies used. Additionally, this technique increases tissue structural orientation data acquisition speed by threefold. They have applied this new approach to in vivo volar forearm data, from which $\mu_a$ and $\mu_s'$ maps were derived, showing agreement with 3-phase SFDI. They have also shown that SOI values obtained from a structural orientation phantom using our new approach are comparable to those obtained using 3-phase SFDI. Further, the demodulation technique may be optimized to allow for the implementation of a real-time SFDI platform.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of extracting and imaging spatial frequency information, comprising:
   obtaining a biological sample;
   utilizing an instrument configured to provide a dataset from the biological sample; and
   extracting the dataset for spatial frequency information from the biological sample illuminated by a single pattern projection by filtering and/or transforming the image data collected from the biological sample,
   wherein patterned light and the Hilbert transform is used to extract spatial frequency information as a means for implementation of a real-time Spatial Frequency Domain Imaging (SFDI) platform for diagnosis.

2. The method of claim 1, wherein transforming the image data includes utilizing a spiral phase function in 2D Fourier space.

3. The method of claim 2, wherein transforming the image data comprises a 2D Hilbert transform technique.

4. The method of claim 1, wherein the instrument comprises a structured illumination device.

5. The method of claim 4, wherein the structured illumination device comprises a Spatial Frequency Domain Imaging (SFDI) device.

6. The method of claim 1, wherein the spatial frequency information comprises optical properties of the sample.

7. The method of claim 1, wherein the spatial frequency information comprises structural orientation contrast of the sample.

8. The method of claim 1, wherein the sample is a biological sample.

9. The method of claim 1, wherein the sample is in vivo tissue.

10. The method of claim 1, wherein the sample is turbid media.

11. The method of claim 1, wherein the spatial frequency information is extracted directly from a subject.

12. The method of claim 1, wherein the spatial frequency information is extracted from a human.

13. The method of claim 1, wherein the spatial frequency information is extracted from an animal.

14. The method of claim 1, wherein the spatial frequency information is extracted from a plant.

15. The method of claim 1, wherein the spatial frequency information is extracted from an organism.

16. The method of claim 1, wherein a single frame of data corresponds to each AC spatial frequency.

17. The method of claim 1, wherein the spatial frequency information is extracted from rotated sinusoidal patterns.

18. The method of claim 1, wherein the spatial frequency information includes tissue structural orientation.

19. An apparatus for diagnosis, comprising:
    means for projecting spatially modulated light on a biological sample; and
    means for extracting spatial frequency information from the biological sample using a two-dimensional (2D) Hilbert transform technique,
    wherein patterned light and the 2D Hilbert transform technique is used to extract spatial frequency information as a means for implementation of a real-time Spatial Frequency Domain Imaging (SFDI) platform in diagnosis.

20. The apparatus of claim 19, wherein the means for projecting spatially modulated light comprises a Spatial Frequency Domain Imaging (SFDI) device.

21. The apparatus of claim 19, further comprising an endoscope.

22. The apparatus of claim 19, further comprising a real-time SFDI platform.

* * * * *